United States Patent
Treado et al.

(10) Patent No.: US 7,551,821 B2
(45) Date of Patent: *Jun. 23, 2009

(54) CHEMICAL IMAGING FIBERSCOPE

(75) Inventors: Patrick J. Treado, Pittsburgh, PA (US);
Matthew P. Nelson, Pittsburgh, PA (US); Scott A. Keitzer, Export, PA (US);
Ryan D. Smith, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/744,797

(22) Filed: May 4, 2007

(65) Prior Publication Data

US 2007/0263290 A1   Nov. 15, 2007

Related U.S. Application Data

(63) Continuation of application No. 10/934,885, filed on Sep. 3, 2004, now Pat. No. 7,239,782.

(60) Provisional application No. 60/144,518, filed on Jul. 19, 1999.

(51) Int. Cl.
*G02B 6/06* (2006.01)
*G01J 3/44* (2006.01)
*A61B 1/06* (2006.01)

(52) U.S. Cl. .......................... 385/117; 356/301; 600/181

(58) Field of Classification Search ................. 385/115, 385/116, 117; 356/301; 600/160, 178, 181, 600/182

See application file for complete search history.

(56) References Cited

U.S. PATENT DOCUMENTS 5,041,108 A   8/1991   Fox et al.
5,377,004 A   12/1994  Owen et al.

(Continued)

FOREIGN PATENT DOCUMENTS

WO   95/11624   5/1995

(Continued)

OTHER PUBLICATIONS

Morris, Hoyt and Treado, "Imaging Spectrometers for Fluorescence and Raman Microscopy: Acoustic-Optic and Liquid Crystal Turnable Filters," Applied Spectroscopy, vol. 48, No. 7, (1994), pp. 857-866.

(Continued)

*Primary Examiner*—Alessandro Amari
(74) *Attorney, Agent, or Firm*—Duane Morris LLP

(57) ABSTRACT

A fiberscope device is disclosed which is suitable for video imaging, laser Raman spectroscopy and laser Raman spectroscopic (i.e. chemical) imaging. The fiberscope design minimizes fiber background interference arising from the laser delivery fiber optic and the coherent fiber optic light gathering bundle while maintaining high light throughput efficiency through the use of integrated spectral filters. In the fiberscope design, the laser delivery fiber optic is offset from the coherent fiber optic light gathering bundle. The laser delivery field is captured entirely by the light gathering field of view of the coherent fiber bundle. The fiberscope incorporates spectral filter optical elements that provide environmental insensitivity, particularly to temperature and moisture. The fiberscope is suited to the analysis of a wide range of condensed phase materials (solids and liquids), including the analysis of biological materials such as breast tissue lesions and arterial plaques, in such a manner to delineate abnormal from normal tissues.

42 Claims, 9 Drawing Sheets

U.S. PATENT DOCUMENTS

| | | |
|---|---|---|
| 5,394,499 A | 2/1995 | Ono et al. |
| 5,710,626 A | 1/1998 | O'Rourke et al. |
| 5,862,273 A | 1/1999 | Pelletier |
| 5,866,430 A | 2/1999 | Grow |
| 5,901,261 A | 5/1999 | Wach |
| 5,911,017 A | 6/1999 | Wach et al. |
| 5,974,211 A | 10/1999 | Slater |
| 6,002,476 A | 12/1999 | Treado |
| 6,006,001 A | 12/1999 | Alfano et al. |
| 6,091,872 A | 7/2000 | Katoot |
| 6,222,970 B1 | 4/2001 | Wach et al. |
| 6,485,413 B1 | 11/2002 | Boppart et al. |
| 7,239,782 B1 * | 7/2007 | Treado et al. ............... 385/117 |

OTHER PUBLICATIONS

Morris, Hoyt and Treado, "Liquid Crystal Turnable Filter Raman Chemical Imaging," Applied Spectroscopy, vol. 50, No. 6, (Jun. 1996) pp. 805-811.

Skinner, Cooney, Sharma and Angel, "Remote Raman Microimaging Using an AOTF and a Spatially Coherent Microfiber Optical Probe," Applied Spectroscopy, vol. 50, No. 8 (1996), pp. 1007-1014.

\* cited by examiner

CHEMICAL IMAGING FIBERSCOPE

This application claims the benefit of U.S. Provisional Application No. 60/144,518, entitled "Chemical Imaging Fiberscope" filed Jul. 19, 1999.

FIELD OF THE INVENTION

The present invention is related to fiberscope probes for spectroscopic and image analysis, and, in particular, to probes useful for both Raman spectroscopy and Raman chemical imaging.

BACKGROUND OF THE INVENTION

Raman chemical imaging combines Raman spectroscopy and digital imaging for the molecular-specific analysis of materials. Raman chemical imaging has traditionally been performed in laboratory settings using research-grade light microscope technology as the image gathering platform. However, Raman chemical imaging is applicable to in situ industrial process monitoring and in vivo clinical analysis. The application of chemical imaging outside the research laboratory has been limited by the lack of availability of stable imaging platforms that are compatible with the physical demands of industrial process monitoring and clinical environments. Both industrial and clinical settings often require compact, lightweight instrumentation suitable for the examination of remote areas that are inaccessible to conventional Raman instrumentation and involve harsh chemicals in hostile environments.

Raman spectroscopy is an analytical technique that is broadly applicable. Among its many desirable characteristics, Raman spectroscopy is compatible with samples in aqueous environments and can be performed on samples undergoing little or no sample preparation. The technique is particularly attractive for remote analysis via the use of optical fibers. By employing optical fibers as light delivery and collection, the light source and light detector can be physically separated from the sample. This remote attribute is particularly valuable in sensing and analysis of samples found in industrial process environments and living subjects.

In a typical fiber-optic-based Raman analysis configuration, one or more illumination fiber-optics deliver light from a light source (typically a laser) through a laser bandpass optical filter and onto a sample. The laser bandpass filter allows only the laser wavelength to pass while rejecting all other wavelengths. This purpose of the bandpass filter is to eliminate undesired wavelengths of light from reaching the sample. Upon interaction with the sample, much of the laser light is scattered at the same wavelength as the laser. However, a small portion of the scattered light (1 in 1 million scattered photons) is scattered at wavelengths different from the laser wavelength. This phenomenon is known as Raman scattering. The collective wavelengths generated from Raman scattering from a sample are unique to the chemistry of that sample. The unique wavelengths provide a fingerprint for the material and are graphically represented in the form of a spectrum. The Raman scattered light generated by the laser/sample interaction is then gathered using collection optics which then direct the light through a laser rejection filter which eliminates the laser light, allowing only Raman light to be transmitted. The transmitted light is then coupled to a detection system via one or more collection fiber-optics.

Previously described Raman fiber optic probe devices have several limitations. First, current fiber-optic-based Raman probes are sensitive to environmental variability. These devices often fail to function properly when the probe is subjected to hot, humid-and/or corrosive environments. Several fundamental differences from current devices have been incorporated into the chemical imaging fiberscope design described here that address the environmental sensitivity issue. First, an outer jacket that is mechanically rugged and resistant to high temperatures and high humidity has been incorporated into the fiberscope design. Second, an optically transparent window that withstands harsh operating environments, has been built into the probe at the fiberscope/sample interface. Normally, incorporation of a window into a probe would introduce a significant engineering problem. As emitted illumination light passes through the window and onto the sample, a portion of this light is back reflected by the window's inner and outer surfaces. In the prior art, this undesired back reflected light is inadvertently introduced into the collection fibers along with the desired Raman scattered light. The back reflected light corrupts the quality of the analysis. This problem is addressed in the current design by careful engineering of the aperture of the collection bundle taking into account the numerical apertures (NA) associated with the collection bundle fibers and collection lenses.

Previous probe designs are also inadequate because of the environmental sensitivity of the spectral filters that are employed in the devices. The Raman chemical imaging fiberscope design of the current invention relies on spectral filter technologies that are remarkably immune to temperature and humidity. Past spectral filters have traditionally been fabricated using conventional thin film dielectric filter technology which are susceptible to temperature and humidity induced degradation in the filter spectral performance. The spectral filters described in the present invention employ highly uniform, metal oxide thin film coating materials such as $SiO_2$, which exhibits a temperature dependent spectral bandshift coefficient an order of magnitude less than conventional filter materials. The improved quality and temperature drift performance of metal oxide filters imparts dramatically improved environmental stability and improved Raman performance under extreme conditions of temperature and humidity.

A final limitation of current probe technologies is that none combine the three basic functions of the chemical imaging fiberscope: (1) video inspection; (2) Raman spectral analysis; and (3) Raman chemical image analysis, in an integrated, compact device.

Raman chemical imaging integrates the molecular analysis capabilities of Raman spectroscopy with image acquisition through the use of electronically tunable imaging spectrometers. Several imaging spectrometers have been employed for Raman chemical imaging, including acousto-optical tunable filters (AOTFs) and liquid crystal tunable filters (LCTFs). For Raman imaging, LCTFs are clearly the instrument of choice based on the following demonstrated figures of merit: spatial resolving power (250 nm); spectral resolving power (<0.1 $cm^{-1}$); large clear aperture (20 mm); and free spectral range (0-4000 $cm^{-1}$). AOTFs and LCFPs are competitive technologies. AOTFs suffer from image artifacts and instability when subjected to temperature changes.

Under normal Raman imaging operation, LCTFs allow Raman images of samples to be recorded at discrete wavelengths (energies). A spectrum is generated corresponding to thousands of spatial locations at the sample surface by tuning the LCTF over a range of wavelengths and collecting images systematically. Contrast is generated in the images based on the relative amounts of Raman scatter or other optical phenomena such as luminescence that is generated by the different species located throughout the sample. Since a spectrum is generated for each pixel location, chemometric analysis tools such as Cosine Correlation Analysis (CCA), Principle Component Analysis (PCA) and Multivariate Curve Resolution (MCR) are applied to the image data to extract pertinent information.

SUMMARY OF THE INVENTION

To address the need for remote chemical inspection technology, a novel flexible fiberscope device has been developed that is Raman chemical imaging capable. The design of the Raman chemical imaging fiberscope has several advantages over the prior art. First, metal oxide dielectric filters are used. These filters are effectively immune to humidity and temperature changes, in stark contrast to traditional dielectric filters.

Second, the Raman chemical imaging fiberscope is shrouded in a jacket that is mechanically rugged. Further, a window is used as an optically transparent boundary separating the sample environment from the optical components in the probe.

Third, an imaging fiber-optic or fiberscope has been incorporated into the design, thereby making the Raman chemical imaging fiberscope better suited for interrogating heterogeneous samples. Visual inspection of the sample surfaces and fluids through the use of imaging fiber optics and digital imaging sensors make in-situ monitoring simpler to implement. Further, the video capabilities of the fiberscope can be used to position and focus the sensor. This is especially critical when deploying Raman sensors in confined environments using robotic systems.

The various aspects of the present invention may be more clearly understood and appreciated from a review of the following detailed description of the disclosed embodiments and by reference to the appended drawings and claims.

DETAILED DESCRIPTION OF THE INVENTION

The Raman chemical imaging fiberscope combines in a single platform a laser beam delivery system to irradiate samples for Raman spectroscopy, an incoherent fiber optic bundle to deliver white light illumination and a coherent fiber bundle suitable for Raman spectral collection, Raman image collection and digital video collection.

Figure 1:
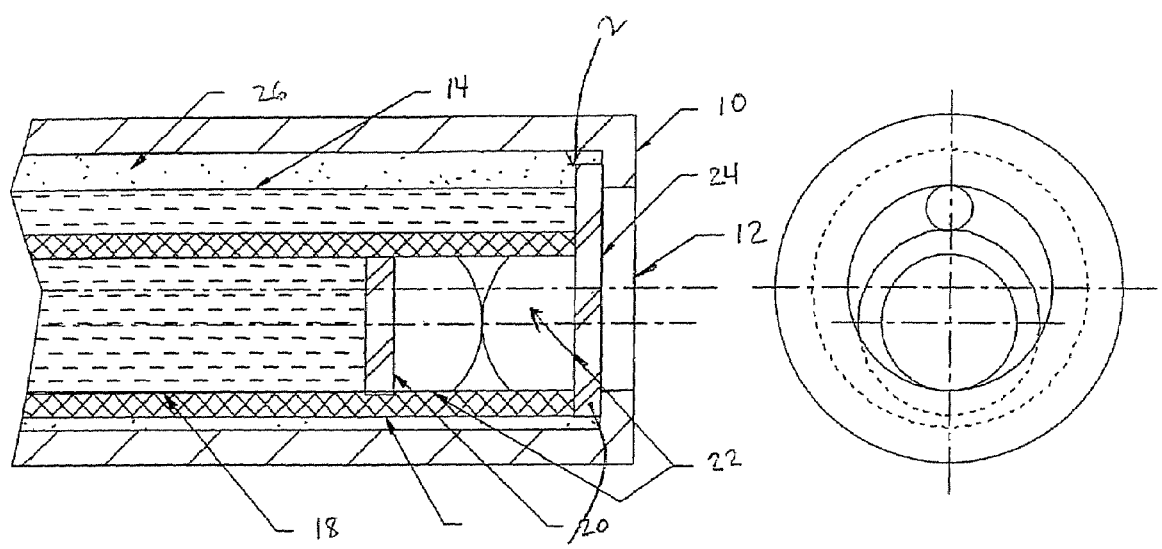
FIG. 1 shows a cross section of the distal end of the Raman chemical imaging fiberscope.

The distal end of the fiberscope is shown in cross-section in FIG. 1. The external housing 10 surrounds the inner core of the fiberscope. The outer jacket is mechanically rugged and immune to hostile sampling environments. At the distal end of the fiberscope is window 12. This window is, in the preferred embodiment, composed of quartz, diamond or sapphire and is used as an optically transparent boundary separating the sample environment from the optical components in the probe.

Laser illumination fiber 14 delivers laser illumination to the sample. This light passes through laser bandpass filter 24, which filters out all wavelengths of light other than the specific wavelength of the laser light transmitted through laser illumination fiber 14. The laser light/sample interaction generates Raman scattering. The scattered light is then collected through the end of the fiberscope. It should be noted that laser bandpass filter 24 is spatially patterned and has optical coatings only on the top portion thereof, such that light exiting laser illumination fiber 14 will be filtered, but scattered light entering the end of the probe will not experience any filtering by laser bandpass filter 24. The portion of laser bandpass filter 24 which receives scattered light from the sample and transmits it to image collection bundle 18 is transparent and performs no filtering function.

After passing through laser band pass filter 24, the scattered light apertured by a spatial filter 28 which acts to restrict the angular field of view of the subsequent optical system. The scattered light is then focused by a pair of lenses 22. The light is then passed through laser reflection filter 20. This filter effectively filters out light having a wavelength identical to the laser light, which was originally transmitted onto the sample through laser illumination fiber 14. After passing through filter 20, the light is transmitted back to the imaging apparatus by the image collection bundle 18.

Successful use of the Raman chemical imaging fiberscope depends on the performance of the spectral filters in humid, elevated-temperature environments. Conventional filters are characterized by the presence of microscale pits and voids. These microstructures absorb water in humid conditions, which cause the thin film matrix to swell and the spectral properties to change, causing the fiber optic probe to be useless. In addition, the coefficients of thermal expansion of traditional dielectric filter thin films (i.e., ZnS or ZnSe) are relatively large. When exposed to elevated temperatures the traditional filter center spectral bandpass shifts, rendering them useless unless a mechanism is devised to rotate the filters and tune them. For example, ZnS has a temperature coefficient of 0.05 nm/° C.

In the preferred embodiment, the filters are metal oxide dielectric filters of the type manufactured by Corion. Metal oxide filters have low coefficients of thermal expansion, and, when exposed to elevated temperature environments the thin film materials comprising the Fabry-Perot cavities do not exhibit gross variation in thin film thickness. As a consequence, the metal oxide filters are insensitive to temperature induced spectral changes, primarily peak transmittance. In addition, the metal oxide thin film coating is also insensitive to humidity which enhances the filter performance when exposed to hostile conditions. The metal oxide filters employ $SiO_2$ as the thin film material, which exhibits a temperature dependent spectral bandshift coefficient of about 0.005 nm/° C.

The imaging fiber optic bundles are preferably high temperature resistant coherent fiber optic bundles, such as those developed by Schoft Glass. These bundles have the unique property that the polyamide cladding employed for typical coherent fiber bundles is leached away (in acid bath) leaving an all-glass fiber bundle that is flexible and can be operated at high temperatures up to about 400° C.

Video imaging of the sample is performed by shining white light on the sample. The white light is transmitted via fibers 26. High quality imaging optics are employed to provide the ability to visually inspect the sample area and to obtain Raman chemical images. Collection lenses 22 focus an image of the sample on the image collection bundle 18. The coherent image collection bundle 18 independently captures white light and Raman scattered photons from the sample surface. The Raman chemical imaging fiberscope provides remote real-time video imaging of the sample when the white light is directed through the image collection bundle 18 to a video CCD. Live video capability assists insertion of the fiberscope and allows visual inspection of the sample area in preparation for spectroscopic analysis. White light for video imaging can be produced by a high power (300 W) Xe lamp.

Figure 2:
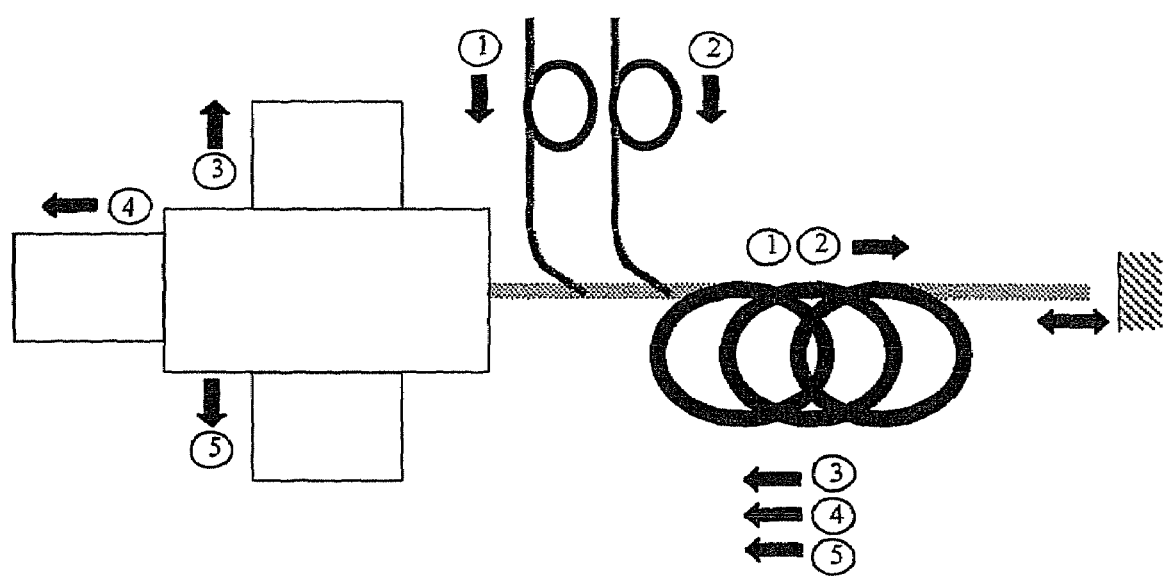
FIG. 2 shows a functional flowchart of pathways for light delivery and collection through the chemical imaging fiberscope.

The Raman scatter is collected through the coherent image collection bundle 18 used to capture the live video. However, laser rejection filter 20 is used to suppress generation of $SiO_2$ Raman background within the image collection bundle 18. As shown in FIG. 2, once collected, the Raman scatter can be diverted in two directions. When sent to a dispersive spectrometer, the Raman chemical imaging fiberscope provides conventional Raman spectral information. The Raman scatter can also be directed through a liquid crystal tunable filter (LCTF) imaging spectrometer onto a sensitive digital CCD. Because the Raman image is maintained through the image collection bundle 18, high quality Raman chemical images can be collected across the fiberscope field of view.

FIG. 2 shows a functional diagram of the Raman chemical imaging fiberscope system. Laser light illumination and white light video illuminations are represented by reference numbers 1 and 2 respectively. These lights enter the fiberscope and are transmitted out the end of the scope to the sample. The Raman spectrum 3, the Raman image 4 and the live video image 5 are transmitted back into the end of the fiberscope. Raman spectrum 3 and Raman image 4 are delivered to processing apparatus which effectively displays the desired information, as described above, while live video image 5 is directed to a monitor for viewing by the user.

Figure 3:
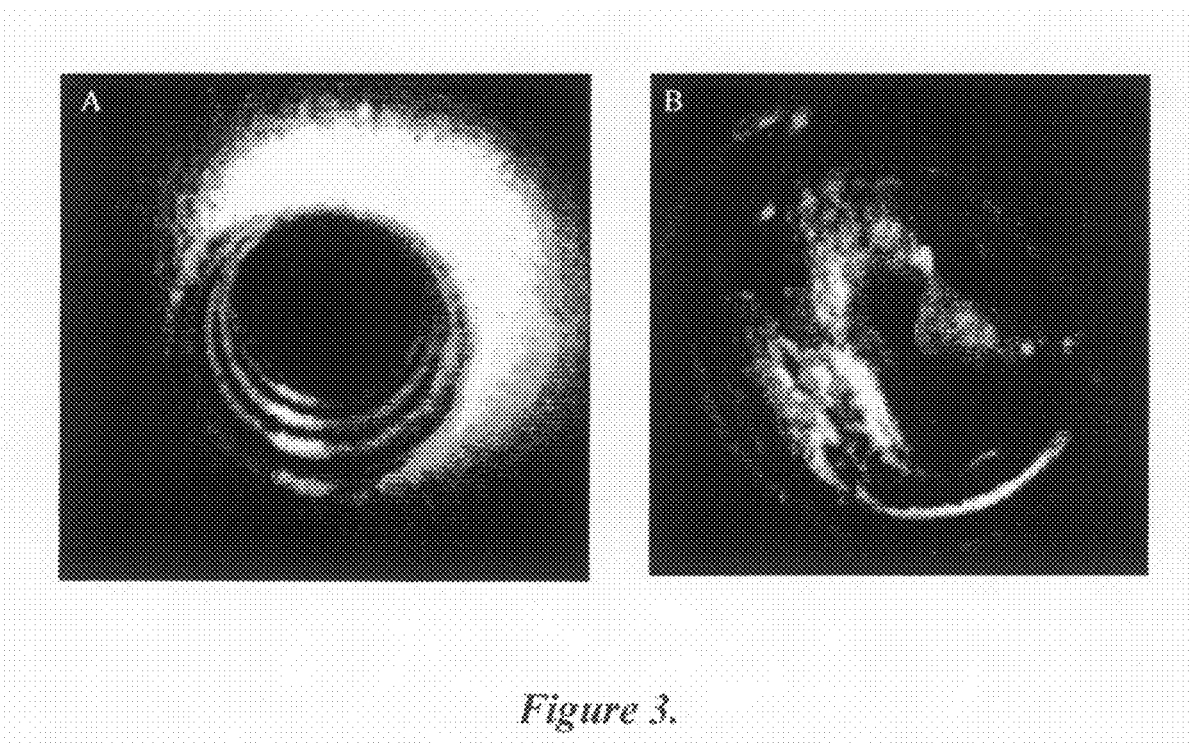
FIGS. 3A and B show the bright field images of the exterior and interior of a bore hole respectively, captured through the chemical imaging fiberscope.

FIG. 3 shows the imaging capabilities of the Raman chemical imaging fiberscope. FIGS. 3A and 3B shows a high fidelity image of the exterior and interior, respectively, of a bore hole. These are bright field images using white light illumination, which show the video performance of the Raman chemical imaging fiberscope. Overall, the Raman chemical imaging fiberscope has a wide field of view and superb image quality.

The video performance of the Raman chemical imaging fiberscope was evaluated by recording a digital image of a USAF 1951 resolution target. The target was illuminated with a diffuse Xe arc lamp source. The output of the Raman chemical imaging fiberscope was optically coupled to a color CCD video camera and bright field images were digitized using a digital frame grabber. To determine the laser spot position and dimension, a diode pumped $Nd:YVO^4$ laser doubled to produce 532 nm light (Millenia II, Spectra Physics) was injected into the laser delivery fiber. The resultant laser spot was projected onto the resolution target substrate at a nominal working distance of 1 cm.

Figure 4:
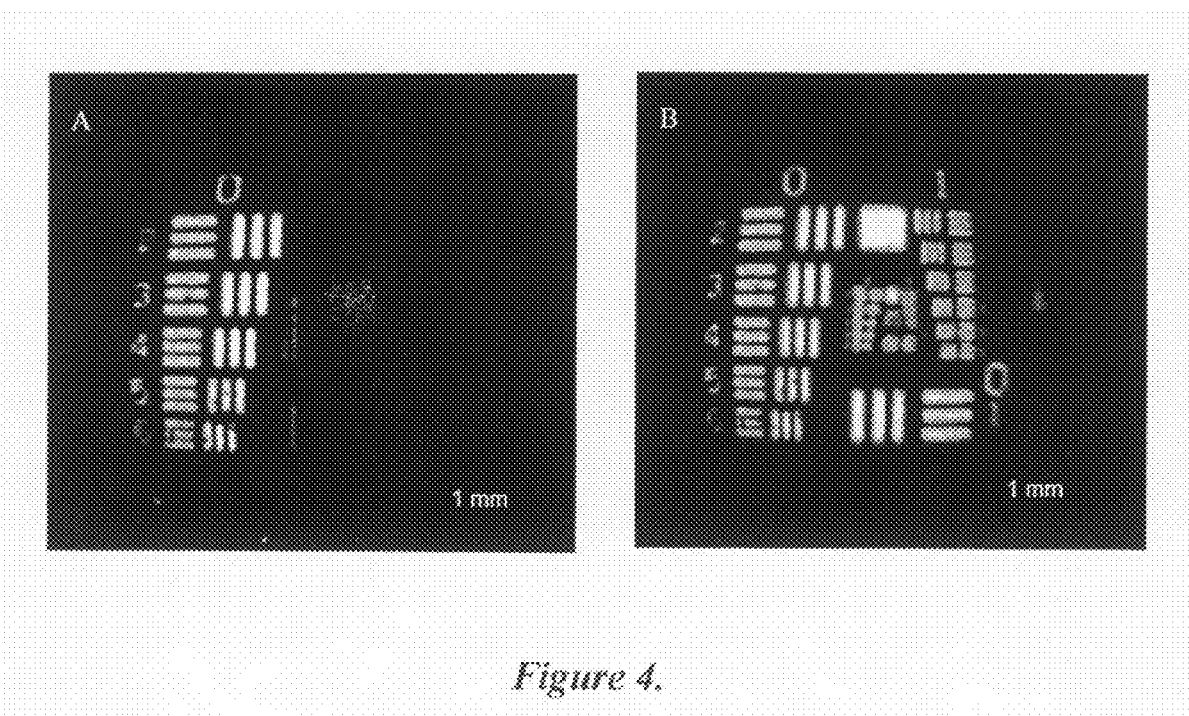
FIG. 4A shows an image of the laser beam projected onto a resolution target images collected through the Raman chemical imaging fiberscope.
FIG. 4B shows an image of the resolution target only for comparison.

FIG. 4 shows resolution target images collected through the Raman chemical imaging fiberscope when back-illuminated with a diffuse Xe source. In FIG. 4A, a 532 nm laser beam was focused into the laser delivery fiber using a high efficiency laser to fiber optic coupler and an image of the laser spot was recorded on a diffuse target superimposed on the resolution target. At a working distance of 1 cm the spot seen near the center of the target image is approximately 2.5 mm in diameter. The laser spot size can be controlled through laser to fiber optic injection strategies and via working distance to the sample. For comparison, FIG. 4B shows the digital image of the USAF resolution target.

As previously described, high performance, environmentally resistant spectral filters are incorporated into the distal end of the flexible Raman chemical imaging fiberscope. Room temperature spectra were acquired to measure the out of band rejection efficiency of the fiberscope using combinations of white light and laser light. Room temperature spectra were acquired to measure the 532 nm laser rejection efficiency during fiberscope collection. Laser rejection is required for the observation of the weak Raman signal and to prevent the inherent Raman scatter of the collection fiber. Xenon light was sent into the collection end of the fiberscope. The output from the viewing end of the fiberscope was measured using a dispersive spectrometer.

Figure 5:
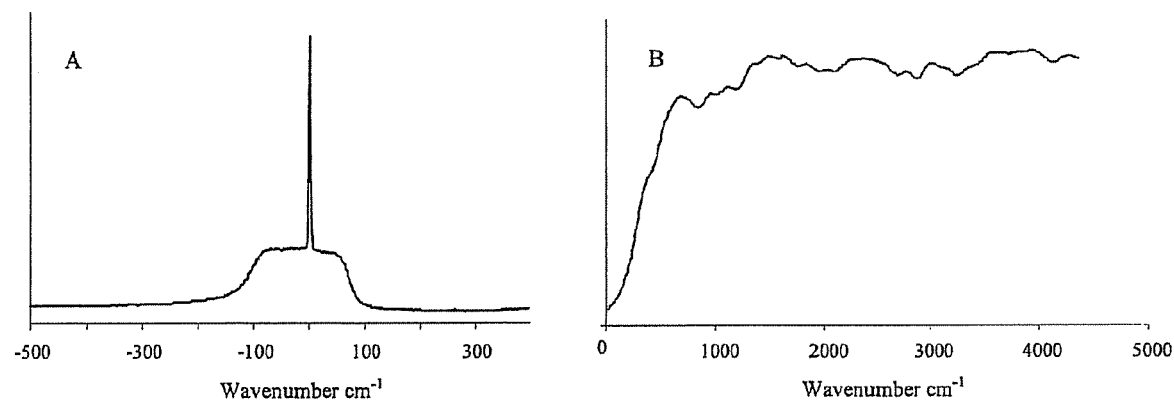
FIG. 5A shows the simultaneous transmission of white light and laser light through the laser delivery fiber optic and laser bandpass filter.
FIG. 5B shows the transmission bandpass through the laser rejection filter and coherent imaging bundle.

FIG. 5 shows transmission spectra collected through the Raman chemical imaging fiberscope. FIG. 5A shows the transmission bandpass through the laser delivery fiber optic under simultaneous Xe white light and 532 nm laser light illumination. From this spectrum, it is apparent that the incorporated bandpass filter sufficiently passes 532 nm light while cutting off transmission above 140 $cm^{-1}$ red-shifted from the laser line. FIG. 5B shows the transmission bandpass through the filter incorporated within the coherent fiber bundle. It is apparent that the incorporated notch filter sufficiently rejects 532 nm light while passing light above 200 $cm^{-1}$ red-shifted from the laser line.

Figure 6:
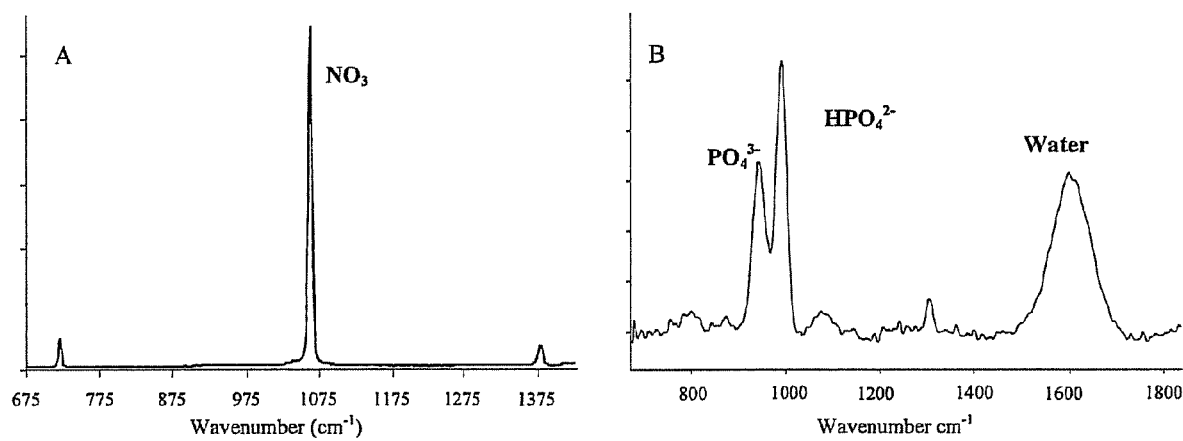
FIGS. 6A and B show Raman spectra of a sodium nitride pellet and a sodium phosphate solution, respectively, captured through the chemical imaging fiberscope.

Dispersive Raman spectra of sodium nitrate and sodium phosphate in aqueous solution collected with the Raman chemical imaging fiberscope are presented in FIG. 6. The sodium nitrate Raman spectrum in FIG. 6A reveals the characteristic nitrate band at 1065 $cm^{-1}$. Note the high signal to background ratio (S/B) and the absence of fiber optic Raman background. In FIG. 6B, the phosphate bands at 945 $cm^{-1}$ and 995 $cm^{-1}$ can be seen.

Room temperature Raman spectra of a sodium nitrate pellet, was collected to assess the Raman collection performance of the Raman chemical imaging fiberscope. The viewing end of the fiberscope was coupled to a dispersive Raman spectrometer. Illumination of the sodium nitrate pellet was provided by injecting laser light into the laser delivery fiber.

High temperature Raman spectra of zirconium oxide were also collected. A furnace was used to heat the sample and distal end of the Raman chemical imaging fiberscope. A thermocouple was used to monitor the temperature at the distal end of the fiberscope. The viewing end of the fiberscope was coupled to a dispersive Raman spectrometer. Illumination of the zirconium oxide pellet was provided by injecting laser light into the laser delivery fiber of the Raman chemical imaging fiberscope.

Figure 7:
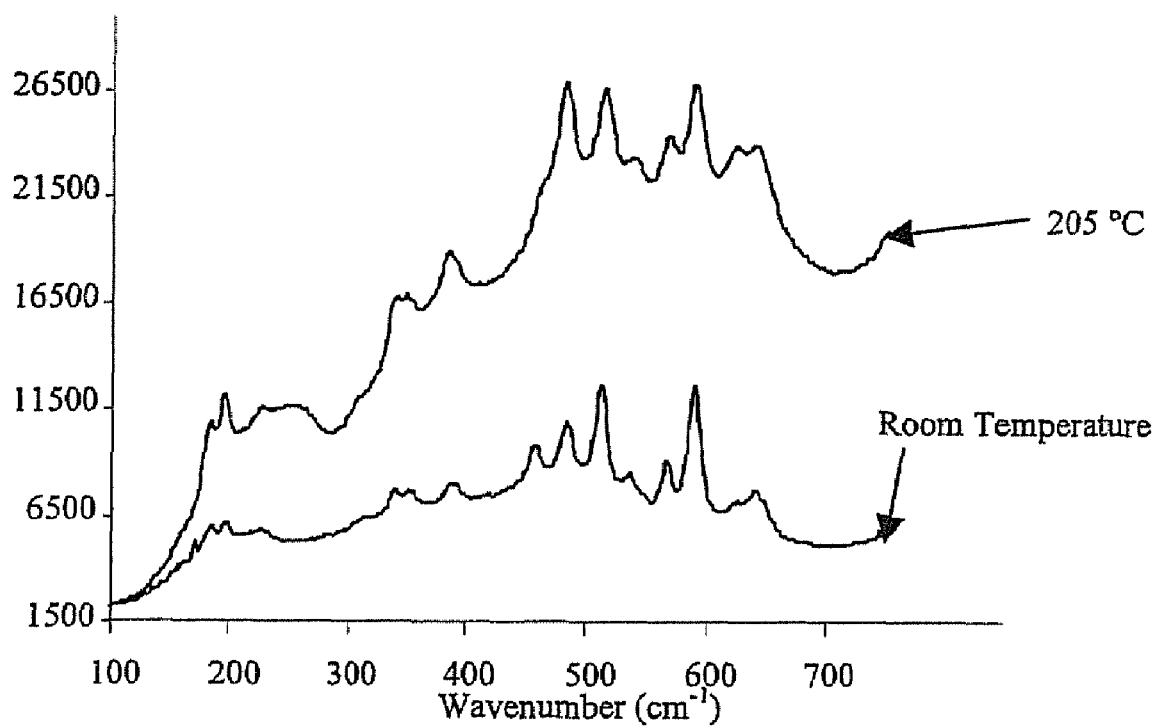
FIG. 7 shows Raman spectra of zirconium oxide collected at room temperature and 205° C. through the chemical imaging fiberscope.

FIG. 7 shows two zirconium oxide spectra—one collected at room temperature (27° C.), the other at 205° C. The Raman features are still discernable in the high temperature spectrum. There is an increase in the overall intensity of the background signal (thermal background) and in the relative intensities of the peaks. Of note, both spectra show Raman features to well within 200 $cm^{-1}$ of the laser line.

Raman chemical image data was collected from an over the counter pharmaceutical tablet containing aspirin (Alka Seltzer, Bayer). The image from the viewing end of the fiberscope was focused onto a CCD camera and an LCTF was inserted into the optical path. Dispersive spectroscopy revealed that the tablet excipient had a Raman band at 1060 $cm^{-1}$. Since this is close to the 1044 $cm^{-1}$ Raman band of aspirin, these two peaks were used for chemical image analysis. A CCD image was collected every 9 $cm^{-1}$ while the LCTF was tuned from 1000 $cm^{-1}$ to 1110 $cm^{-1}$.

Figure 8:
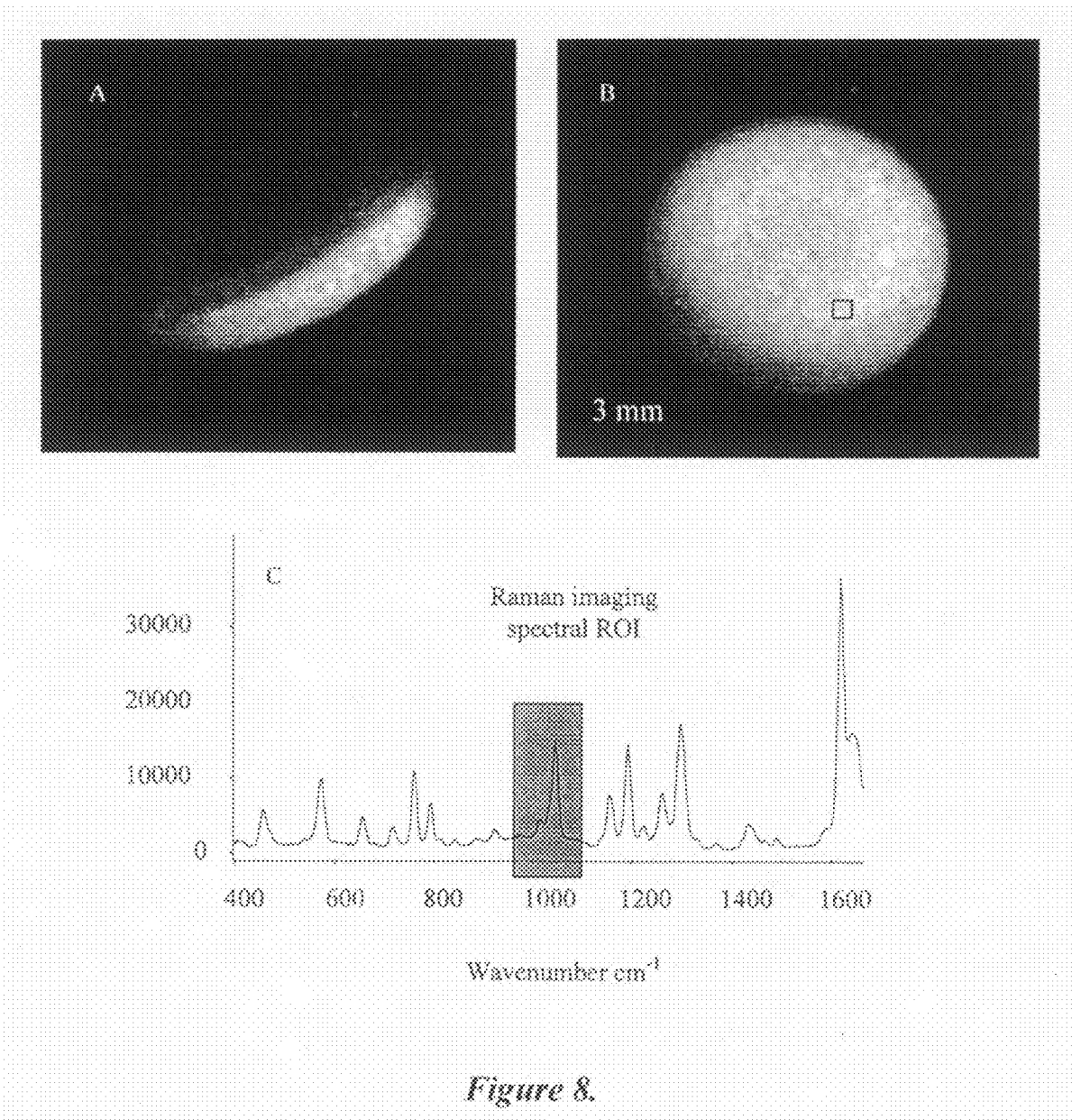
FIGS. 8A and B show bright field images of an aspirin tablet collected through the fiberscope under white light illumination conditions.
FIG. 8C shows a Raman spectrum of the aspirin tablet captured from the boxed region in FIG. 8B and collected with a dispersive Raman spectrometer under Raman spectroscopy conditions.

Images of the tablet collected through the fiberscope using ambient light can be seen in FIGS. 8A and 8B. The box in FIG. 8B shows the region from where the Raman spectrum in FIG. 8C was acquired. FIG. 8C shows a dispersive Raman spectrum dominated by aspirin (acetylsalicylic acid). The box shaded in gray represents the spectral range that was sampled to generate Raman chemical images (see FIG. 9).

The multivariate technique cosine correlation analysis (CCA) was applied to Raman chemical image data using Chemimage software, produced by the assignee of this invention, Chemicon. CCA is a multivariate image analysis technique that assesses similarity in chemical image data sets while simultaneously suppressing background effects when performed in conjunction with normalization of each linearly independent Raman spectra contained in the image dataset. CCA assesses chemical heterogeneity without the need for extensive training sets. CCA identifies differences in spectral shape and effectively provides molecular-specific contrast that is independent of absolute intensity.

Figure 9:
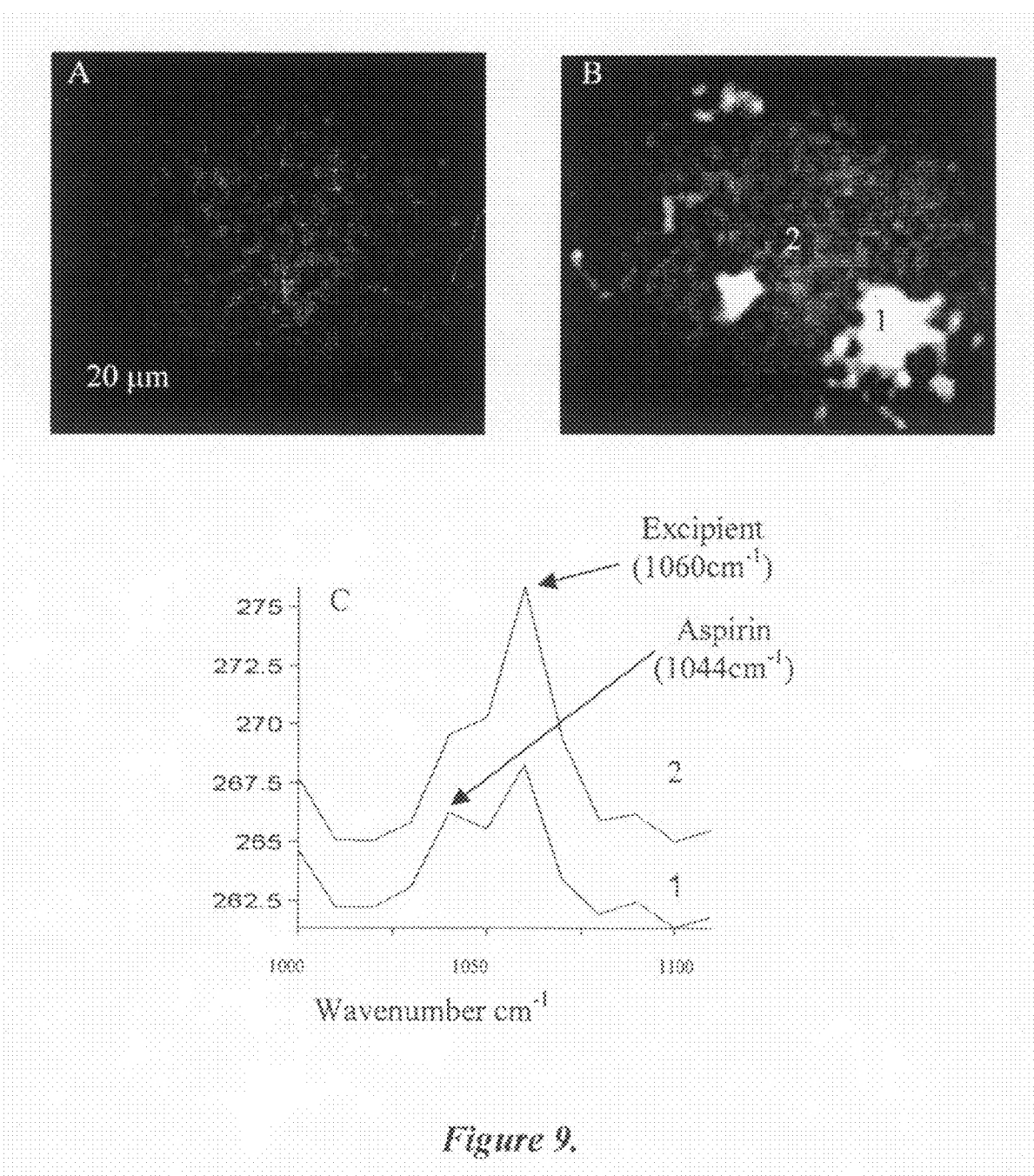
FIG. 9A shows bright field images of a microregion of a tablet containing aspirin collected through the fiberscope under white light illumination conditions.
FIG. 9B shows a Raman chemical image of the same tablet collected through the fiberscope operating under Raman imaging conditions.
FIG. 9C shows representative Raman spectra collected through imaging spectrometer of aspirin and excipient.

FIG. 9 displays the Raman chemical imaging results from the aspirin tablet. FIG. 9A is a bright field image of the sampled area captured through the Raman chemical imaging fiberscope. FIG. 9B is a grayscale Raman chemical image generated using CCA with the brightest regions showing the aspirin component at 1044 $cm^{-1}$ and the darker regions showing the excipient component (calcium carbonate) collected at 1060 $cm^{-1}$. FIG. 9C shows LCTF Raman spectra from regions 1 (localized aspirin) and 2 (excipient), respectively.

In summary, the Raman chemical imaging fiberscope is the first fiberscope technology which incorporates all of the following: laser delivery, white light illumination, video collection, Raman spectral collection and LCTF-based Raman chemical imaging capability within a compact device (the distal end outside diameter of the flexible fiberscope is only 2 mm). The Raman chemical imaging fiberscope is environmental resistant and can be used in a variety of hostile and confined environments over a range of operating temperatures and humidities. Due to its compact dimensions and rugged design, the Raman chemical imaging fiberscope is well suited to in situ industrial monitoring and in vivo clinical applications.

Although the invention was described in the context of a Raman fiberscope probe, the present invention offers the ability to perform other chemical (spectroscopic) imaging techniques such as near infra-red and luminescence chemical imaging.

The present invention has been described in relation to particular embodiments which are intended in all respects to be illustrative rather than restrictive. Alternative embodiments will become apparent to those skilled in the art to which the present invention pertains without departing from its spirit and scope. Accordingly, the scope of the present invention is defined by the appended claims rather than the foregoing description.

We claim:

1. A method of imaging and collecting Raman spectra from a sample, the method comprising:
    transmitting laser light of a specific laser excitation wavelength from a first source to a sample via one or more laser illuminating fibers;
    positioning a first portion of a spectral filter between said one or more laser illumination fibers and said sample for transmitting said laser light of said specific laser excitation wavelength and rejecting light of other wavelengths;
    positioning a second portion of the spectral filter between said sample and a plurality of collection fibers for transmitting wavelengths of light other than said specific laser excitation wavelength; and
    receiving light scattered from said sample via said plurality of collection fibers;
    wherein the spectral filter is spatially patterned into the first portion for filtering said laser light and into the second portion for transmitting light scattered or reflected by said sample to said plurality of collection fibers.

2. The method of claim 1 wherein said plurality of collection fibers are arranged in a coherent bundle.

3. The method of claim 1 wherein at least one of said first or second portions of the spectral filter exhibit environmental insensitivity to temperature and humidity.

4. The method of claim 1 further comprising positioning one or more lenses between said sample and said plurality of collection fibers.

5. The method of claim 1 wherein said first or second portions of the spectral filter are composed of a filter type selected from a group consisting of dielectric, holographic and rugate spectral filters.

6. The method of claim 1 further comprising positioning a spatial filter between said sample and said collection fibers for controlling an angular field of view of said collection fibers.

7. The method of claim 1 further comprising:
    holding the distal end of a housing in proximity to said sample wherein said housing encloses said spectral filter, said one or more laser illuminating fibers, and said plurality of collection fibers;
    directing the output of the collection fibers under white light illumination conditions to a live video camera via a first link;
    directing the output under laser illumination conditions to a Raman spectrometer via a second link;
    directing the output under laser illumination conditions to a Raman chemical imaging spectrometer and detector via a third link.

8. The method of claim 1 wherein a housing encloses said spectral filter, said one or more laser illuminating fibers and said plurality of collection fibers.

9. The method of claim 8 wherein a window is disposed at the distal end of said housing.

10. The method of claim 9 wherein said window is composed of a material selected from a group consisting of quartz, diamond and sapphire.

11. The method of claim 1 further comprising selectably transmitting white light from a second source to said sample with a plurality of white light illumination fibers.

12. The method of claim 11 wherein said plurality of collection fibers are arranged in a coherent bundle.

13. The method of claim 12 wherein at least one of said first or second portions of the spectral filter exhibit environmental insensitivity to temperature and humidity.

14. The method of claim 13 further comprising positioning one or more lenses between said sample and said plurality of collection fibers.

15. The method of claim 11 wherein a housing encloses said spectral filter, said one or more laser illuminating fibers, said plurality of white light illumination fibers and said plurality of collection fibers.

16. The method of claim 15 wherein a window is disposed at the distal end of said housing.

17. The method of claim 16 wherein said window is composed of a material selected from a group consisting of quartz, diamond and sapphire.

18. The method of claim 11 wherein said spectral filter exhibits environmental insensitivity to temperature and humidity.

19. The method of claim 11 further comprising positioning a spatial filter between said sample and said collection fibers for controlling an angular field of view of said collection fibers.

20. A method of imaging and collecting Raman spectra from a sample with a chemical imaging spectroscope, the method comprising:
   transmitting laser light of a specific laser excitation wavelength from a first source to a sample via one or more laser illuminating fibers;
   positioning a first portion of a spectral filter between said one or more laser illumination fibers and said sample for transmitting said laser light of said specific laser excitation wavelength and rejecting light of other wavelengths;
   positioning a second portion of the spectral filter between said sample and a plurality of collection fibers for transmitting wavelengths of light other than said specific laser excitation wavelength;
   positioning a spatial filter between said sample and said collection fibers for controlling an angular field of view of said collection fibers;
   positioning one or more lenses between said sample and said plurality of collection fibers; and
   receiving light scattered from said sample via said plurality of collection fibers;
   wherein the spectral filter is spatially patterned into the first portion for filtering said laser light and into the second portion for transmitting light scattered or reflected by said sample to said plurality of collection fibers.

21. A method of illuminating and collecting light from a sample, the method comprising:
   transmitting laser light of a specific laser excitation wavelength from a first source to a sample with one or more laser illuminating fibers via a first optical path;
   transmitting white light from a second source to said sample with a plurality of white light illumination fibers via a second optical path;
   receiving light scattered or reflected from said sample with said plurality of collection fibers;
   transmitting said scattered or reflected light to an imaging apparatus via a third path;
   wherein said one or more laser illumination fibers, said plurality of white light illumination fibers, said plurality of collection fibers are disposed in a housing wherein said first optical path is different from said second optical path and wherein said first and third optical paths each include a spectral filter.

22. The method of claim 21 wherein said first optical path comprises said laser illumination fibers, a first portion of a spectral filter, and a window disposed at the distal end of said housing.

23. The method of claim 22 wherein said second optical path comprises said white light illumination fibers and said window.

24. The method of claim 23 wherein said third optical path comprises said window and a second portion of said spectral filter.

25. The method of claim 24 further comprising
   filtering said laser light with said first portion of the spectral filter;
   wherein said first portion of said spectral filter is spatially patterned for filtering said laser light and said second portion of the spectral filter is transparent for transmitting light scattered or reflected by said sample to said collection fibers.

26. The method of claim 25 wherein said third optical path comprises said window, said second portion of said spectral filter, a spatial filter, a lens, a reflection filter, and said collection fibers.

27. The method of claim 21 wherein said first and second optical paths are each different from said third optical path.

28. The method of claim 21 wherein a first portion of said spectral filter is spatially patterned for filtering said laser light and a second portion of said spectral filter is transparent for transmitting light scattered or reflected by said sample to said collection fibers.

29. The method of claim 21 wherein said spectral filter exhibits environmental insensitivity to temperature and humidity.

30. The method of claim 21 wherein said spectral filter is composed of a filter type selected from a group consisting of dielectric, holographic and rugate spectral filters.

31. The method of claim 21 wherein said plurality of collection fibers are arranged in a coherent bundle.

32. The method of claim 21 further comprising:
   disposing one or more lenses in said third optical path.

33. The method of claim 21 wherein a window is disposed at a distal end of said housing.

34. The method of claim 33 wherein said window is composed of a material selected from a group consisting of quartz, diamond and sapphire.

35. The method of claim 21 wherein said imaging apparatus comprises a spectrometer.

36. The method of claim 35 wherein said spectrometer is a Raman spectrometer.

37. The method of claim 21 wherein said imaging apparatus includes a tunable filter.

38. The method of claim 37 wherein said tunable filter is a liquid crystal tunable filter.

39. The method of claim 21 further comprising producing a Raman image of said sample.

40. The method of claim 21 further comprising producing a chemical image of said sample.

41. The method of claim 21 wherein said imaging apparatus comprises a charge-coupled device.

42. The method of claim 41 wherein said charge-coupled device is a video charge-coupled device.

* * * * *